United States Patent
DiCaprio et al.

(10) Patent No.: US 6,176,843 B1
(45) Date of Patent: Jan. 23, 2001

(54) CATHETER WITH DISTAL MANIFOLD PREP VALVE/MANIFOLD

(75) Inventors: Fernando DiCaprio, Mendota Heights; David J. Blaeser, Champlin, both of MN (US)

(73) Assignee: SciMed Life Systems, Inc., Maple Grove, MN (US)

( * ) Notice: Under 35 U.S.C. 154(b), the term of this patent shall be extended for 0 days.

(21) Appl. No.: 09/208,145

(22) Filed: Dec. 9, 1998

(51) Int. Cl.[7] ................................................. A61M 29/00
(52) U.S. Cl. ................................ 604/99.03; 604/167.04
(58) Field of Search .............................. 604/99.01, 99.02, 604/99.03, 99.04, 97.01, 236, 247, 167.01, 167.2–167.04, 249; 606/194

(56) References Cited

U.S. PATENT DOCUMENTS

| | | | |
|---|---|---|---|
| 5,100,385 | * | 3/1992 | Bromander ......................... 604/99.03 |
| 5,224,933 | | 7/1993 | Bromander . |
| 5,545,133 | | 8/1996 | Burns et al. . |
| 5,674,193 | * | 10/1997 | Hayes ............................... 604/236 X |
| 5,695,468 | | 12/1997 | Lafontaine et al. . |
| 5,785,685 | | 7/1998 | Kugler et al. . |

FOREIGN PATENT DOCUMENTS 0 299 158 A1   1/1989   (EP) .

* cited by examiner

Primary Examiner—A. T. Nguyen
(74) Attorney, Agent, or Firm—Crompton, Seager & Tufte, LLc

(57) ABSTRACT

An inflatable balloon catheter having a guide wire lumen, an inflation lumen, and a one-way valve disposed within the inflation lumen, the one-way valve allowing fluid flow from the guide wire lumen into the inflation lumen and balloon. One method for preparing the catheter for use includes blocking the guide wire lumen proximal port and injecting inflation fluid into the guide wire lumen distal port. The injected fluid flows through the one-way valve into the inflation lumen and exits through the inflation lumen proximal port. One catheter includes a proximal switchable valve having bleed and inflation positions. This catheter provides a small distal profile and allows for bleeding the catheter while inflation equipment is attached to the catheter.

10 Claims, 1 Drawing Sheet

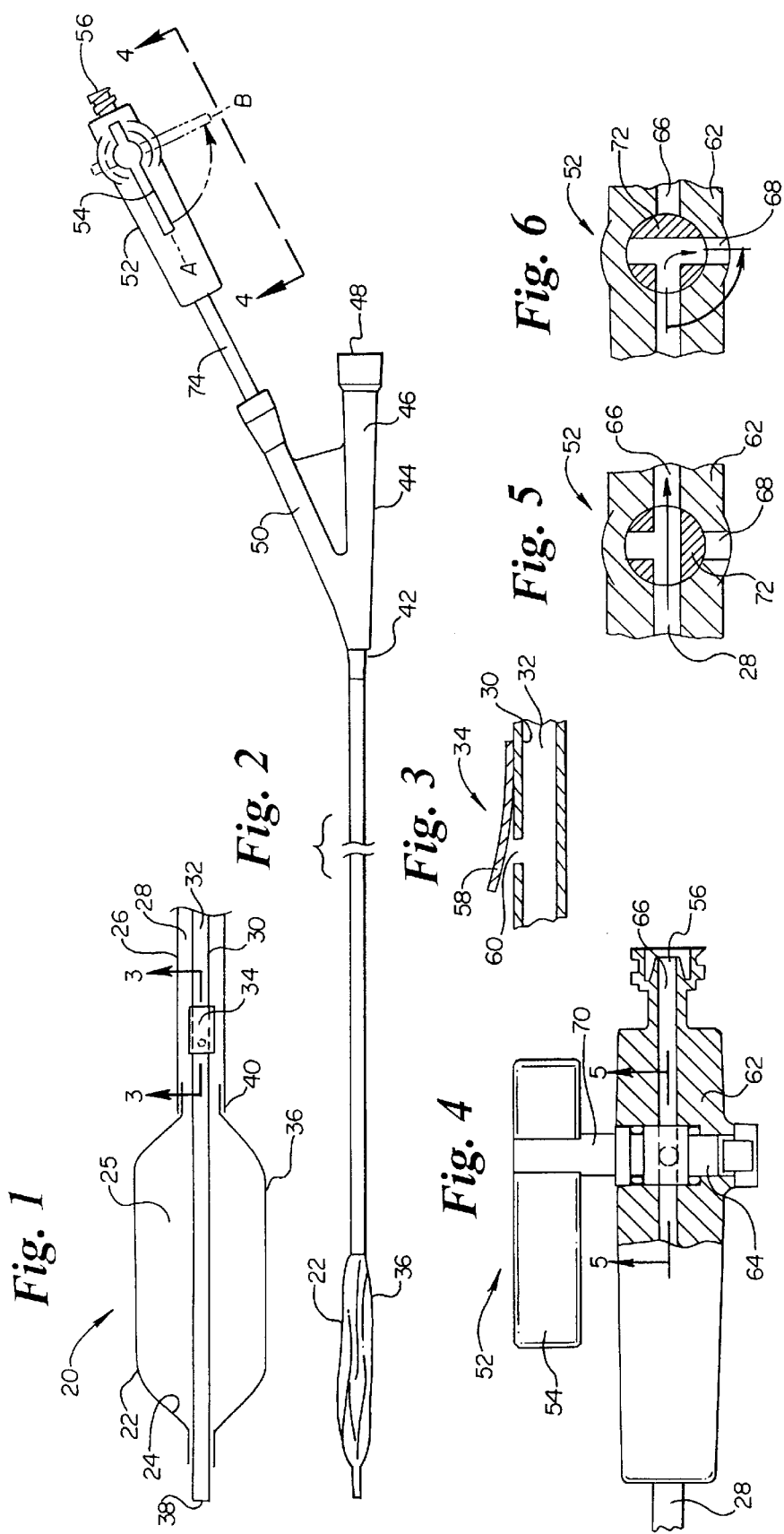

CATHETER WITH DISTAL MANIFOLD PREP VALVE/MANIFOLD

RELATED U.S. APPLICATIONS

The present invention is related to U.S. Pat. No. 5,785,685, filed Mar. 5, 1997, entitled "Balloon Catheter with Improved Pressure Sources".

FIELD OF THE INVENTION

The present invention is related generally to methods for preparing inflatable balloon catheters for use. Specifically, the present invention relates to methods and devices for infusing balloon catheters with inflation fluid and expelling air prior to use.

BACKGROUND OF THE INVENTION

Balloon dilatation catheters are used in medical procedures in which a body vessel is dilated. One such procedure is angioplasty, in which a stenosed, narrowed blood vessel is widened using an inflatable balloon catheter. Balloon catheters are also used for stent delivery. The balloon catheter typically includes an elongate, flexible shaft having an inflatable balloon disposed near the catheter distal end. The shaft commonly includes an inflation lumen within. The inflation lumen is in fluid communication with the balloon such that balloon inflation is accomplished by injecting fluid under pressure into the inflation lumen. The catheter can also have a guide wire lumen either extending the length of the shaft in "over the wire" catheters or extending only the length of the balloon or the length of the balloon and part of the shaft in "single operator exchange" catheters. The catheters are long enough to extend from an insertion point near the groin or arm to the coronary arteries.

During treatment, the inflation lumen is filled with inflation fluid under pressure, causing balloon expansion within the narrowed region to be dilated. Prior to treatment, the catheter must be prepared for use. Preparation includes preloading the inflation lumen and balloon with inflation fluid. Preparations also include purging the catheter inflation lumen and balloon of air. Balloon catheters have commonly had a single orifice for both injecting inflation fluid into the catheter and releasing air from the catheter. Specifically, the inflation lumen proximal port is typically the only orifice through which inflation fluid passes.

Inflation fluid can be injected into the inflation lumen proximal port while the catheter is held vertically such that the balloon is much lower than the proximal port. Alternately, inflation fluid can be drawn in by pulling a vacuum from the distal end of the catheter. Some air bubbles rise through the sinking inflation fluid, the inflation fluid partially adhering to tube walls due to surface tension. It would be more desirable to have both an inflation fluid inlet and outlet orifice, allowing for inflation fluid entry through one orifice and air and fluid exit through the other orifice.

Bromander, in U.S. Pat. No. 5,100,385, proposes placing a one-way valve between the guide wire lumen and inflation lumen. Bromander discusses using the proximal guide wire port for entry of inflation fluid, and using the proximal inflation lumen port for exit of inflation fluid. In the Bromander design, bleeding the catheter while having inflation injection equipment attached can be difficult as the inflation fluid entry and bleed ports are one in the same. The Bromander design also positions the one-way valve within the balloon. This is less than optimal, as the distally disposed balloon preferably has a small profile and locating the valve within the balloon can increase this profile. The balloon, during preparation, is preferably tightly wrapped and constrained within a balloon protector, leaving little room for movement of the one-way valve mechanism.

What would be desirable is an improved balloon catheter capable of being rapidly purged of air and filled with inflation fluid prior to use. An improved method for rapidly purging and filling a balloon catheter with inflation fluid would be desirable.

SUMMARY OF THE INVENTION

The present invention includes an inflatable balloon catheter adapted to be rapidly purged of air and prepared for use, including being filled with inflation fluid. One catheter according to the present invention includes a proximal region, a distal region, an inflatable balloon having an envelope, a guide wire lumen in fluid communication with the balloon envelope, a one-way valve allowing fluid flow from the guide wire lumen into the inflation lumen, and a switchable valve in fluid communication with the inflation lumen. The switchable valve is preferably disposed at the inflation lumen proximal end, and has a bleed position and an inflation position. One embodiment switchable valve also has a closed or blocking position, blocking fluid flow from the inflation lumen proximal end.

In one embodiment, the guide wire lumen is defined by a guide wire tube which is coaxially disposed within an inflation tube defining the inflation lumen for most of the length of the inflation tube. In another embodiment, the guide wire tube is enveloped by an inflation lumen preferably having a crescent shaped cross section. In yet another embodiment, a "single operator exchange" embodiment, the guide wire lumen is substantially coextensive with the balloon, not being substantially co-extensive with the inflation lumen proximal of the balloon.

One method for preparing a catheter for use includes providing a catheter as previously described, preferably blocking the guide wire lumen proximal port, forcing inflation fluid under pressure into the guide wire lumen distal port, thereby allowing the inflation fluid to flow through the one way valve into the inflation lumen and balloon. The inflation fluid is allowed to flow proximally out of the inflation lumen proximal port. Methods utilizing catheters having a proximal switchable valve can include setting the valve to a bleed position prior to forcing the inflation fluid from the catheter and setting the valve to an inflation position prior to inflating the balloon with inflation fluid. Alternatively, a check valve could be used. In switchable valves having a closed position, the valve can be closed and the catheter set aside between preparation and use.

BRIEF DESCRIPTION OF THE DRAWINGS

FIG. 1 is a fragmentary, longitudinal, cross-sectional view of a distal end of a balloon catheter having a guide wire tube, an inflation tube, and a one-way valve therebetween;

FIG. 2 is a fragmentary perspective view of the catheter of FIG. 1, including a proximal manifold and switchable valve;

FIG. 3 is a fragmentary, side, cross sectional view of a guide wire tube having a one-way valve;

FIG. 4 is a fragmentary, cutaway side view of the switchable valve of FIG. 2;

FIG. 5 is a fragmentary, cross-sectional top view of the switchable valve of FIG. 2 in the inflation position; and FIG. 6 is a fragmentary, cross-sectional top view of the switchable valve of FIG. 2 in the bleeding position.

DETAILED DESCRIPTION OF THE PREFERRED EMBODIMENT

FIG. 1 illustrates an inflatable balloon catheter 20 having a distal region 36 and a balloon 22 having an envelope 24 defining a balloon interior 25. Balloon 22 is illustrated in an inflated state. Balloon envelope 24 terminates proximally in a proximal waist 40. An inflation tube 26 having an inflation lumen 28 is secured to balloon proximal waist region 40. Extending within balloon 22 and inflation tube 26 is a guide wire tube 30 defining a guide wire lumen 32 within. Guide wire lumen 32 terminates distally in a distal port 38. A one-way valve 34 is fixedly attached to guide wire tube 30 within inflation lumen 28. Positioning one-way valve 34 within inflation lumen 28, rather than within balloon envelope 24, allows for a smaller profile of balloon 22 prior to inflation. It is important that balloon 22, disposed at the distal end of balloon catheter 20, has a small profile, to allow the catheter distal end to be maneuvered through narrowed, stenosed vessel regions. One-way valve 34 allows flow of inflation fluid from guide wire lumen 32 into inflation lumen 28 but inhibits flow from inflation lumen 28 into guide wire lumen 32. Inflation lumen 28, being in fluid communication with balloon interior 25, allows inflation of balloon 22 once fluid is within the inflation lumen.

Referring now to FIG. 2, balloon catheter 20 is further illustrated, having distal region 36 and a proximal region 42. Catheter proximal region 42 includes a manifold 44 having a guide wire arm 46 and an inflation arm 50. Guide wire arm 46 terminates proximally in a proximal port 48. A guide wire can be inserted through proximal guide wire port 48 and further into the guide wire lumen. Inflation arm 50 is in fluid communication with a switchable valve 52 having a proximal, inflation port 56, and a lever 54 shown in an inflation position indicated at "A." Lever 54 can also assume a bleeding position, indicated at "B." In some embodiments, lever 54 can be turned to a third position (not requiring illustration) which puts switchable valve 52 into a closed or blocked position, in which inflation lumen 28 is blocked at the proximal end, allowing neither bleeding nor inflation.

In a preferred embodiment, manifold 44 separates the guide wire tube and inflation tube. In the embodiment of FIG. 2, an intermediate inflation tube 74 extends between valve 52 and manifold 44. In the embodiment illustrated, a guide wire can project proximally from manifold guide wire proximal port 48, while inflation lumen 28 angles away from the guide wire lumen in manifold 44. This manifold configuration allows an inserted guide wire to remain straight, requiring only the inflation lumen to bend. It can be appreciated that guide wire lumen 28 could be shortened to make a single operator exchange (S.O.E.) embodiment of the catheter.

Referring now to FIG. 3, one-way valve 34 is illustrated in more detail. In the embodiment illustrated, valve 34 has a flap 58 and a flow orifice 60. Flap 58 is biased to close over flow orifice 60 such that flow through the orifice is greatly restricted in the closed position. During the preparation procedure, inflation fluid is injected under pressure into guide wire tube 30. When there is sufficient pressure within guide wire tube 30 to overcome the bias of flap 58, flap 58 opens, allowing fluid flow out of guide wire lumen 32 and into the inflation lumen. Flap 58 is preferably biased to such an extent that a pressure greater than about one atmosphere is required to open the flap. This degree of bias strength is preferred as it may be desirable to apply a vacuum to inflation lumen 28 to evacuate air from the inflation lumen and balloon. If flap 58 is not sufficiently strong, flap 58 could open under vacuum, causing flap 58 to open, resulting in a loss of vacuum. During treatment, inflation fluid is injected under pressure into the inflation lumen. Pressure within the inflation lumen brings pressure to bear on flap 58, causing flap 58 to close over orifice 60, stopping or greatly restricting flow.

Referring now to FIG. 4, switchable valve 52 is illustrated, including handle 54 connected by a valve stem 70 to a valve cock 64 which in mounted within a valve seat 62. Valve cock 64 rotates within seat 62 and is closely matched to seat 62 such that fluid flow between valve cock 64 and valve seat 62 is negligible. A valve inflation channel 66 is illustrated, extending proximally from valve cock 64.

Referring now to FIGS. 5 and 6, valve cock 64 and seat 62 of switchable valve 52 are illustrated from the top in more detail. FIG. 5 illustrates valve 52 in inflation position corresponding to handle position "A." In this position, inflation lumen 28 is in fluid communication with valve inflation channel 66. FIG. 6 illustrates valve 52 in bleed position corresponding to handle position "B." In this position, inflation lumen 28 is in fluid communication with a valve bleed channel 68, allowing fluid in inflation lumen 28 to be bleed. A valve cock hemispheric portion 72 blocks bleed channel 68 when valve 52 is in the inflation position and blocks valve inflation channel 66 when valve 52 is in the bleed position. In yet another position, caused by valve cock 64 being rotated 180 degrees from the position illustrated in FIG. 6, hemispheric portion 72 locks inflation lumen 28, effectively sealing the inflation lumen and allowing no fluid flow in or out of the catheter through valve 52.

In use, inflatable balloon catheter 20 can be prepared for use by placing a balloon protector over balloon 22 if one is not already present. A balloon protector is typically a cylindrical sheath that fits closely over an uninflated balloon. Guide wire lumen 32 can be plugged or blocked proximally, preferably at manifold guide wire proximal port 48. If the catheter were designed as a S.O.E. catheter, the proximal guide wire lumen outlet would be disposed distally of the proximal end of the catheter. The proximal outlet would thus be plugged rather than port 48. A threaded plug can be used for this purpose if manifold proximal port 48 is threaded, otherwise an elastomeric or metallic plug can be forced into manifold proximal port 48. Optionally, a vacuum can be applied to inflation lumen 28 to evacuate any air in inflation lumen 28 and balloon interior 25. Vacuum can be applied at switchable valve 52 through either bleed channel 68 or inflation channel 66.

Guide wire lumen distal port 38 can be mated with an inflation fluid delivery device. One such device is a syringe having an elastomeric or rubber tip adapted to fit tightly within distal port 38. Inflation fluid can be delivered under pressure through guide wire lumen distal port 38. Inflation fluid cannot flow through guide wire lumen proximal port 48, as this port has been effectively blocked. The inflation fluid is thus forced through one-way valve 34 into inflation lumen 28 and into balloon envelope interior 25. One-way valve 34, being disposed proximally of balloon 22, allows balloon 22 to have a smaller profile. Balloon envelope interior 25 may have a very small volume, due in part to being constrained by a balloon protector.

The injected inflation fluid flows through inflation lumen 28 to switchable valve 52, which, being in the bleed position, allows inflation fluid to exit through bleed channel 68. Balloon catheter 20 is preferably in a vertical position during this process, have balloon 22 below and switchable valve 52 above. Having balloon catheter 20 in this position allows air bubbles to rise to switchable valve 52 and be purged from the catheter. In one method, handle 54 is also switched to the inflation position, allowing air to escape and inflation fluid to fill valve inflation channel 66 as well as any attached inflation fluid injection device.

Once sufficient inflation fluid has left through bleed channel 68, the injection of inflation fluid can be stopped. Handle 54 can be either left in bleed position or switched to inflation position. Leaving handle 54 in bleed position can allow for a last minute, final bleed or purge of the catheter prior to use. In one catheter preparation method, switchable valve 52 is switched to a closed or blocking position, the inflation fluid source removed from guide wire lumen distal port 38, and the catheter optionally set aside in a non-vertical orientation. Closing switchable valve 52 in this manner allows catheter preparation to be performed well ahead of a treatment procedure, and in some circumstances, by a person less skilled than the physician inserting the catheter within the patient. Upon removal of the inflation fluid source, inflation fluid present in guide lumen 32 can be allowed to leak from guide wire lumen distal port 38. In one method, the inflation fluid injection source is left attached to guide wire lumen distal port 38, so as to allow for last minute injection of and bleeding of inflation fluid. The wire lumen can also be flushed with saline.

After catheter 20 has been bleed for the final time, the plug can be removed from guide wire lumen proximal port 48. Catheter 20 now has air substantially removed from balloon interior 25 and inflation lumen 28. Balloon interior 25 and inflation lumen 28 are also substantially filled with inflation fluid. The proximal end of a guide wire can be inserted into guide wire lumen distal port 38 and threaded through guide wire lumen 32, exiting through manifold guide wire arm proximal port 48. After balloon 22 has been advanced over the guide wire and across a vessel region to be treated, handle 54 can be switched to inflation position and inflation fluid injected through proximal inflation port 56. As bleeding can be accomplished through valve bleed channel 68, an inflation fluid injection device such as a syringe, can be filled and secured to manifold proximal port 56 long before inflation of balloon 22 is required.

In another method, switchable valve 52 is not required at all. In this method, the aforementioned bleed and inflation ports are one in the same. In this method, inflation fluid is injected through the guide wire lumen distal port but is allowed to exit through a proximal inflation port serving a function similar to that of proximal port 56. One bleeding has been completed, an inflation device such as a syringe can be attached, if not already present, and filled with inflation fluid. The catheter is now ready for use, having been bleed, purged of air, and secured to an inflation device.

Numerous characteristics and advantages of the invention covered by this document have been set forth in the forgoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An inflatable balloon catheter comprising:
    a shaft having a proximal end and a distal end;
    a guide wire lumen being defined through at least a portion of said shaft;
    an inflatable balloon disposed at said shaft distal end, said balloon having an interior;
    an inflation lumen, said inflation lumen being in fluid communication with said balloon interior,
    said guide wire lumen having a one-way valve on that portion of the lumen which is disposed outside of the balloon, allowing flow of fluid from said guide wire lumen into said inflation lumen and balloon interior; and
    a switchable valve in fluid communication with said inflation lumen having a bleeding position allowing fluid flow from said inflation lumen and an inflating position allowing fluid flow into said inflation lumen.

2. An inflatable balloon catheter as recited in claim 1, wherein said inflation lumen has a proximal region and said switchable valve is disposed near said inflation lumen proximal region.

3. An inflatable balloon catheter as recited in claim 1, wherein said guide wire lumen is substantially co-extensive with said balloon and said guide wire lumen is not substantially co-extensive with said inflation lumen proximal of said balloon.

4. An inflatable balloon catheter as recited in claim 1, wherein said guide wire lumen is disposed within said balloon interior.

5. A method for preparing a catheter for use comprising the steps of:
    providing a catheter including
    a shaft having a proximal end and a distal end;
    a guide wire lumen being defined through at least a portion of said shaft and having a proximal port and a distal port;
    an inflatable balloon disposed at said shaft distal end, said balloon having an interior;
    an inflation lumen having a proximal port, said inflation lumen being in fluid communication with said balloon interior,
    said guide wire lumen having a one-way valve on that portion of the lumen which is disposed outside of the balloon, allowing flow of fluid from said guide wire lumen into said inflation lumen;
    preventing fluid flow from said guide wire lumen proximal port; and
    forcing inflation fluid under pressure into said guide wire lumen distal port, such that inflation fluid is forced through said one-way valve into said inflation lumen, such that some air in said inflation lumen is forced out by said inflation fluid under pressure.

6. A method for preparing a catheter for use as recited in claim 5, wherein said catheter includes a switchable valve in fluid communication with said inflation lumen having an inflating position allowing fluid flow into and out of said inflation lumen and a closed position preventing fluid flow into and out of said inflation lumen, further comprising:
    setting said switchable valve into said inflation position, such that said inflation fluid is allowed to escape from said inflation lumen; and
    closing said switchable valve, such that inflation fluid is contained within said inflation lumen by said switchable valve.

7. A method for preparing a catheter for use as recited in claim 5, further comprising:
    applying a vacuum to said inflation lumen prior to forcing said inflation fluid through said guide wire lumen, such that some air in said inflation lumen is removed.

8. A method for preparing a catheter for use as recited in claim 5, wherein said preventing step includes blocking said guide wire lumen proximal port.

9. A method for preparing a catheter for use as recited in claim 5, wherein said catheter includes a switchable valve in fluid communication with said inflation lumen having a bleeding position allowing fluid flow from said inflation lumen and an inflating position allowing fluid flow into said inflation lumen, further comprising:

setting said switchable valve into said bleeding position, such that said inflation fluid is allowed to escape from said inflation lumen.

10. A method for preparing a catheter for use as recited in claim 9, wherein said switchable valve has a closed position, further comprising the step of closing said valve after bleeding said catheter, such that inflation fluid is contained within said inflation lumen by said switchable valve.

* * * * *